(12) United States Patent
Kitayama

(10) Patent No.: US 7,395,554 B2
(45) Date of Patent: Jul. 8, 2008

(54) MASK FOR EYES

(75) Inventor: Hidehiro Kitayama, Tokyo (JP)

(73) Assignee: Nawari Trading Co., Ltd., Tokyo (JP)

( * ) Notice: Subject to any disclaimer, the term of this patent is extended or adjusted under 35 U.S.C. 154(b) by 37 days.

(21) Appl. No.: 11/230,244

(22) Filed: Sep. 19, 2005

(65) Prior Publication Data
US 2006/0064793 A1 Mar. 30, 2006

(30) Foreign Application Priority Data
Sep. 30, 2004 (JP) ............... 2004-313075

(51) Int. Cl.
*A61F 9/04* (2006.01)

(52) U.S. Cl. .................. 2/15; 2/9; 2/12; 2/440; 2/441; 2/433; 2/206; 2/426; 128/206.23; 602/17; 132/319; 607/109

(58) Field of Classification Search ............ 2/9, 2/15, 12, 440, 441, 433, 426, 206; 602/17; 132/319; 607/109
See application file for complete search history.

(56) References Cited

U.S. PATENT DOCUMENTS

| | | | | |
|---|---|---|---|---|
| 1,743,510 A | * | 1/1930 | Zickmantel | 2/15 |
| 2,765,789 A | * | 10/1956 | Schmierer | 604/308 |
| 2,891,252 A | * | 6/1959 | Lazo | 2/15 |
| 4,872,217 A | | 10/1989 | Kitayama | |
| 5,435,006 A | | 7/1995 | Kitayama | |
| 5,628,772 A | * | 5/1997 | Russell | 607/109 |
| 5,673,432 A | | 10/1997 | Kitayama | |
| 6,537,308 B2 | * | 3/2003 | Burkhart | 607/109 |
| 2006/0156449 A1 | * | 7/2006 | Shows | 2/69 |
| 2006/0218688 A1 | * | 10/2006 | Cheng | 2/12 |

FOREIGN PATENT DOCUMENTS

JP 06-237955 8/1994

* cited by examiner

*Primary Examiner*—Gary L. Welch
*Assistant Examiner*—Alissa J Tompkins
(74) *Attorney, Agent, or Firm*—Bucknam and Archer

(57) ABSTRACT

A mask for eyes is disclosed to include a mask body, a support member formed of an elastic material and fixedly fastened to the mask body at the back, the support member having a thin flap containing a natural mineral stone powder or blocks that emits negative ions, far infrared rays, electrons and radioactive rays to produce Holmishis Effect, and two fastening members for securing the mask body to the user's ears.

2 Claims, 3 Drawing Sheets

MASK FOR EYES

BACKGROUND OF THE INVENTION

1. Field of the Invention

The present invention relates to masks and more particularly, to a mask for eyes that has a natural mineral stone powder contained in a thin flap thereof for producing Holmishis Effect to stimulate the circulation of blood around the user's eyes.

2. Description of the Related Art

Japanese Patent No. 7-51138 discloses a mask for eyes. According to this design, the mask comprises a mask body, which is formed of a soft material and has pores in the two eye portions thereof. Through the pores, the user can see the outside. This design of mask is simply to mask the user's eyes. It does no help to the user's health.

SUMMARY OF THE INVENTION

The present invention has been accomplished under the circumstances in view. It is therefore the main object of the present invention to provide a mask for eyes, which provides Holmishis Effect to stimulate the circulation of blood around the user's eyes.

To achieve this and other objects of the present invention, the mask for eyes comprises a mask body, which has two eye portions and a plurality of pores in the eye portions, a support member, which is formed of an elastic material and fixedly fastened to the back side of the mask body around said eye portions, and two fastening members, which are respectively provided at two distal ends of the mask body for fastening to the user's ears, wherein the support member comprises a thin flap containing a natural mineral stone powder, the thin flap having two openings corresponding to the eye portions of the mask body.

The natural mineral stone powder emits at least one of the substances including negative ions, far infrared rays, electrons and radioactive rays that stimulate the circulation of blood around the user's eyes without producing any side effects.

Further, the support member comprises a plurality of inside pockets that accommodated blocks formed of said natural mineral stone powder.

DETAILED DESCRIPTION OF THE PREFERRED EMBODIMENT

Figure 1:
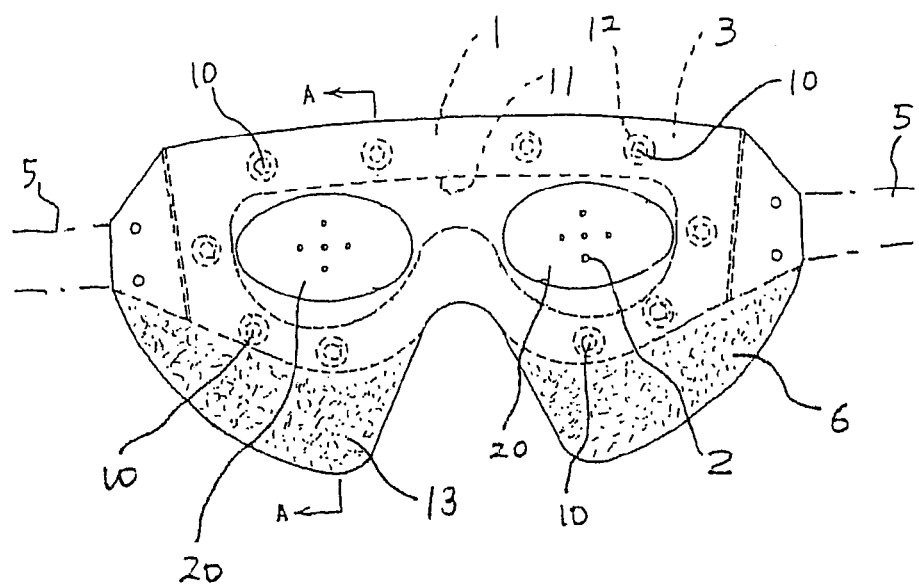
FIG. 1 is a schematic rear view of a mask for eyes according to the present invention.

Referring to FIG. 1, a mask for eyes in accordance with the present invention is shown comprising a soft mask body 3 and a support member 1. The mask body 3 has two eye portions 20 corresponding to the user's eyes, and a plurality of pores 2 in the eye portions 20. The support member 1 is fixedly fastened to the back side of the mask body 3 around the eye portions 20, comprising a hollow annular cover shell 1a and an elastomer 1b stuffed in the cover shell 1a.

Figure 2:
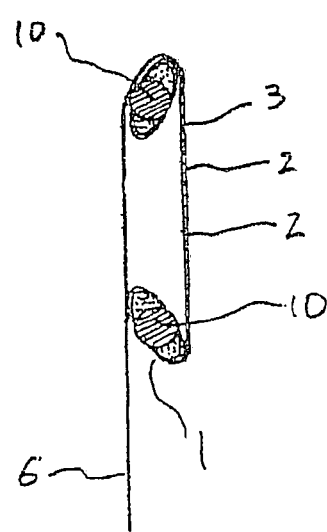
FIG. 2 is a sectional view taken along line A-A of FIG. 1.
Figure 6:
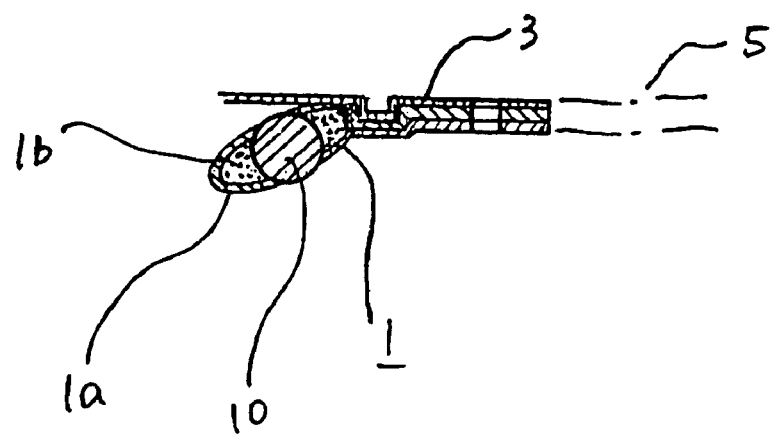
FIG. 6 is a sectional view in an enlarged scale taken along line B-B of FIG. 5.

As shown in FIG. 2 and FIG. 6, the support member 1 has the outer diameter thereof sealed to the border area of the mask body 3 by a thermal compression. The inner diameter of the support member 1 is a free end. Further, two fastening members 5 are provided at the two distal ends of the mask body 3 for securing the mask to the user's ears.

Figure 3:
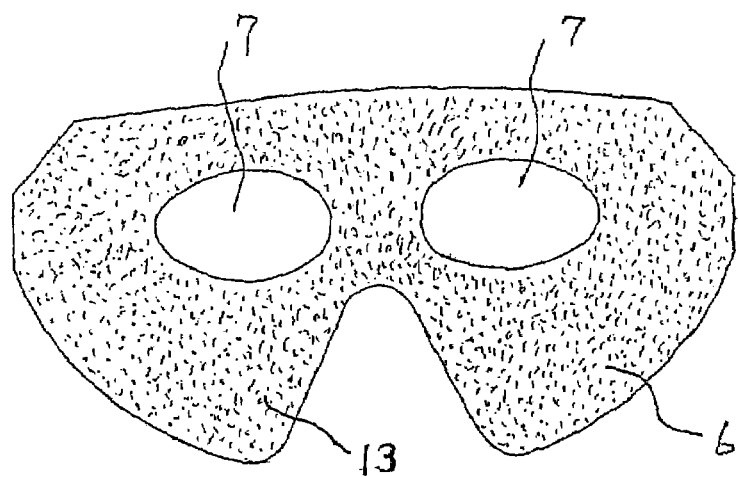
FIG. 3 is a rear view of the thin flap for the mask for eyes according to the present invention.
Figure 4:
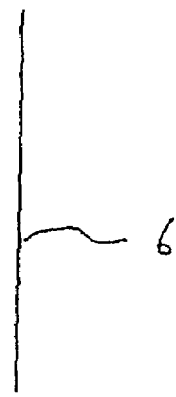
FIG. 4 is a side view of FIG. 3.
Figure 5:
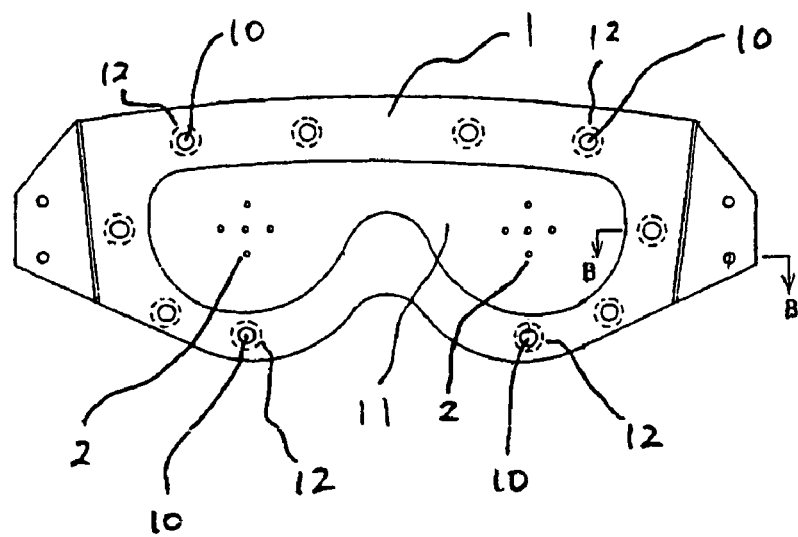
FIG. 5 is a schematic rear view of the mask after removal of the thin flap of FIG. 1 according to the present invention.

As shown in FIG. 3 and 4, a thin flap 6 depends from the inside surface of the support member 1, i.e., the thin flap 6 suspends from the upper part of the support member 1, having two openings 7 corresponding to the pores 2 of the mask body 3. The thin flap 6 is made out of a fabric (cloth or nonwoven fabric) or resin in the shape of a thin sheet member containing or impregnated with natural mineral stone (such as waste stone for Uranium mineral., minerals containing rare elements, etc.) fine powder, designated 13, that constantly emit negative ions, far infrared rays, electrons, and a small amount of radioactive rays (γ-ray, β-ray, α-ray).

According to Holmishis Effect disclosed by Professor T. D of University of Missouri in 1982, the radioactive rays emitted by the natural mineral stone powder contained in the thin flap 6 can improve the functioning of the immunological system of human beings. More particularly, the radiation of the natural mineral stone powder contained in the thin flap 6 is very helpful to the movement and health of the body.

There are many acupuncture points around the eyes of a human being. The thin flap 6 is kept in contact with the area around the user's eyes. The radioactive rays, infrared ray and electrons stimulate the circulation of blood in the user's vessels around the eyes not only with the radioactive rays.

The aforesaid natural mineral stone powder can be made in blocks 10 set in inside pockets 12 inside the support member 1. The support member 1 has an elongated opening 11 through which the user can access to the inside pockets 12 and the blocks 10. These blocks 10 can be shaped like a ball or flat plate member. Further, the blocks 10 may be eliminated from the thin flap 6.

Although particular embodiments of the invention have been described in detail for purposes of illustration, various modifications and enhancements may be made without departing from the spirit and scope of the invention. Accordingly, the invention is not to be limited except as by the appended claims.

LIST OF REFERENCE NUMBERALS

1 support member
2 pores
3 soft mask body
5 soft mask body
6 thin flap
7 openings
10 blocks
11 elongated opening
12 inside pockets
20 eye portions

The invention claimed is:

1. A mask for eyes comprising:
   a mask body (3) having two eye portions (20) substantially corresponding to the user's eyes, said eye portions having a plurality of pores (2);
   a support member (1) formed of an elastic material fixedly fastened at a first side to a side of said mask body around said eye portions;

two fastening members (5) respectively provided at two distal ends of said mask body for fastening to the user's ears; and a thin flap (6) depending from a second side of said support member having two eye openings (7) corresponding to the eye portions of the mask body so that no part of said thin flap contacts the user's eyes, said thin flap contacting the area of the user's face around the user's eyes and containing or being impregnated with a natural mineral stone powder which emits at least one of the substances including negative ions, far infrared rays, electrons and radioactive rays;

whereby the circulation of blood in the area of the user's face around the user's eyes contacted by said thin flap is stimulated.

2. The mask for eyes as claimed in claim 1, wherein said support member comprises a plurality of inside pockets that accommodate blocks formed of said natural mineral stone powder.

\* \* \* \* \*